United States Patent
Bogner et al.

(10) Patent No.: US 9,969,617 B2
(45) Date of Patent: May 15, 2018

(54) MATERIAL SYSTEM CONTAINING ENDOPEROXIDE WITH ADAPTION OF DECOMPOSITION, AND APPLICATIONS

(76) Inventors: Udo Bogner, Regensburg (DE);
Günther Bernhardt, Schierling (DE);
Günther Knör, Österreich (DE)

(*) Notice: Subject to any disclaimer, the term of this patent is extended or adjusted under 35 U.S.C. 154(b) by 0 days. days.

(21) Appl. No.: 13/384,749

(22) PCT Filed: Jul. 21, 2010

(86) PCT No.: PCT/EP2010/060594
§ 371 (c)(1),
(2), (4) Date: Jan. 18, 2012

(87) PCT Pub. No.: WO2011/009903
PCT Pub. Date: Jan. 27, 2011

(65) Prior Publication Data
US 2012/0148480 A1  Jun. 14, 2012

(30) Foreign Application Priority Data
Jul. 21, 2009  (DE) .................. 10 2009 034 279

(51) Int. Cl.
*C01B 13/02* (2006.01)
*A61K 31/357* (2006.01)
*A61K 41/00* (2006.01)

(52) U.S. Cl.
CPC ........ *C01B 13/0225* (2013.01); *A61K 31/357* (2013.01); *A61K 41/0052* (2013.01); *C01B 13/02* (2013.01)

(58) Field of Classification Search
None
See application file for complete search history.

(56) References Cited

U.S. PATENT DOCUMENTS

| 4,436,715 A | 3/1984 | Schaap et al. ................ 423/579 |
| 5,486,274 A * | 1/1996 | Thetford et al. ........... 204/157.5 |
| 2003/0195144 A1* | 10/2003 | Svendsen et al. ................ 514/8 |

FOREIGN PATENT DOCUMENTS

| AU | 548020 | 11/1985 |
| WO | WO 0108660 A2 * | 2/2001 |

OTHER PUBLICATIONS

Turro, Generation, Diffusivity, and Quenching of Singlet Oxygen in Polymer Matrixes Investigated via Chemiluminescence Methods, J. Phys. Chem., 85, 3014-3018 (1981).*

(Continued)

*Primary Examiner* — Melissa S Swain
(74) *Attorney, Agent, or Firm* — Hayes Soloway P.C.

(57) ABSTRACT

This disclosure relates to the release of singlet oxygen by thermally activated decomposition of aromatic endoperoxide molecules in material systems [e.g. polymer (nano) particles or polymer films]. Due to the short lifespan and diffusion length of singlet oxygen, the technical problem is that the majority of the decomposition may only take place if the singlet oxygen molecules can reach the target region. For example, either the penetration of the polymer particles into the cancer cells to be killed, or the settlement of bacteria on an implant coated with the polymer film, must be accomplished. It is necessary to allow adaptation of the time progression of the decomposition for the application. The adaptation is performed by chemically and/or physically modifying the functional structures present in the material system, each made of the molecule forming the endoperoxide and at least one adjacent molecule or the cage formed by all adjacent molecules. Potential applications are in pharmacy and medicine, as well as in production technology.

23 Claims, 3 Drawing Sheets

(56) References Cited

OTHER PUBLICATIONS

Niu, Yields of Singlet Molecular Oxygen from Peroxyl Radical Termination, J. Am Chem. Soc. 114, 165-172 (1992).*
International Search Report issued for corresponding application No. PCT/EP2010/060594, dated Jul. 27, 2011 (12 pgs).
Gollwitzer, Hans,"Eine resorbierbare Poly-D,L-Laktid-Beschichtung zur Ausrüstung medizinischer Implantate," Dissertation, Technische Universität München, 2002, abstract only (1 pg).
Grinholc et al., "Bactericidal effect of photodynamic therapy against methicillin-resistant *Staphylococcus aureus* strain with the use of various porphyrin photosensitizers," Acta Biochimica Polonica, vol. 54, No. Mar. 2007, pp. 665-670 (7 pgs).
Ziegler, Andreas S., "Nanopartikel-pharmazeutische „Zwerge" mit Know-how, MMP 31, 2008, pp. 455-468 (14 pgs).
Wasserman et al., Photooxidation of Methylnaphthalenes, J. Org. Chem, vol. 70, No. 1, 2005, pp. 105-109 (5 pgs).
Borisov et al., "Precipitation as a simple and versatile method for preparation of optical nanochemosensors," Talanta, 2009, pp. 1322-1330, abstract only (1 pg).
International Search Report issued in related application No. PCT/EP2010/060594, dated Jul. 27, 2011 (15 pgs).
Kalz, Franz-Peter, "Untersuchungen für die Anwendung von aromatischen Endoperoxiden in Liposomen and Polymeren zur Tumortherapie," Dissertation zur Erlangung des Doktorgrades der Naturwissenschaften, Sep. 2006 (116 pgs).
Turro et al., "Generation, diffusivity, and quenching of singlet oxygen in polymer matrixes investigated via chemiluminescence methods," The Journal of Physical Chemistry, Bd. 85, Nr. 20, Oct. 1981 (5 pgs).
Kazakov et al., "Chemiluminescence during decomposition of 1,4-dimethylnaphthalene endoperoxide on the silica gel and alumina surface," Russian Chemical Bulletin, Bd. 56, Nr. 2, Feb. 2007 (6 pgs).
Wasserman et al., "Photooxidation of Methylnaphthalenes," The Journal of Organic Chemistry, Bd. 70, Nr. 1, Jul. 2005 (5 pgs).
O'Neill et al., "Lewis acid catalysed rearrangements of unsaturated bicyclic [2.2.n] endoperoxides in the presence of vinyl silanes; access to novel Fenozan B0-7 analogues," Tetrahedron Letters, Bd. 46, Nr. 17, Apr. 2005 (4 pgs).
Niu et al., "Yields of singlet molecular oxygen from peroxyl radical termination," Journal of the American Chemical Society, Bd. 114, Nr. 1, Jan. 1992 (8 pgs).
Otsu et al., "An abortive apoptotic pathway induced by singlet oxygen is due to the suppression of caspase activation," Biochemical Journal, Bd. 389, Nr. 1, Jul. 2005 (10 pgs).
Nagaoka et al., "Specific inactivation of cysteine protease-type cathepsin by singlet oxygen generated from naphthalene endoperoxides," Biochemical and Biophysical Research Communications, Bd. 331, Nr. 1, May 2005 (9 pgs).
Scharffetter-Kochanek et al., "Singlet oxygen induces collagenase expression in human skin fibroblasts," FEBS Letters, Bd. 331, Nr. 3, Oct. 1993 (3 pgs).
European Office Action (w/machine translation) issued in application 10 737 857.2, dated Jul. 11, 2016 (19 pgs).
Posavec et al., "Functionalized derivatives of 1,4-dimethylnaphthalene as precursors for biomedical applications: synthesis, structures, spectroscopy and photochemical activation in the presence of dioxygen," Organic & Biomolecular Chemistry, vol. 10, No. 35, Jul. 2012, pp. 7062-7069 (8 pgs).
Ichimura et al., "A molecular cushion for isomerization," Nature Materials, vol. 4, Mar. 2005, pp. 193-194 (2 pgs).
Evans et al., "The generic enhancement of photochromic dye switching speeds in a rigid polymer matrix," Nature Materials, vol. 4, Mar. 2005, pp. 249-253 (5 pgs).
Hiemenz et al., "Polymer Chemistry: The Basic Concepts," CRC Press, 1984, synopsis only (2 pgs).

* cited by examiner

MATERIAL SYSTEM CONTAINING ENDOPEROXIDE WITH ADAPTION OF DECOMPOSITION, AND APPLICATIONS

FIELD OF THE INVENTION

The present invention relates to a method for producing singlet oxygen by decomposition of endoperoxide molecules in material systems, and use of the said method.

BACKGROUND OF THE INVENTION

In the prior art singlet oxygen is already used in the pharmaceutical field, for example in photodynamic therapy. For this purpose, before the therapy a photosensitising substance, a so-called sensitiser, is administered which accumulates in higher concentration in the tumour tissue than in normal tissue. The sensitiser is excited by irradiation with light, and in the presence of oxygen it can generate singlet oxygen which causes lethal oxidative damage, damaging membrane lipids for example. Because of the interaction of sensitiser and irradiation due to (laser) light the range of applications of the PDT is restricted because of the limited depth of penetration of the therapeutic light. Therefore PDT is preferred for local treatment of superficial carcinomas on the skin or endoscopically accessible hollow organs.

Therefore the object of the present invention is to use the release of singlet oxygen ($^1O_2$) to kill specific biological objects, in particular cells in tumour therapy, such as for example cancer cells, or resistant germs for example by antimicrobial treatment). Because of the short lifespan of singlet oxygen the technically most important problem is that the distance between the production site and the site of action (that is to say the target region in the interior or on the surface of the cell) must be kept very small. This distance depends upon the particular medium in which the singlet oxygen should diffuse into the target region and will generally be less than 1 µ.

SUMMARY OF THE INVENTION

The idea underlying the present invention is that in the production of singlet oxygen due to the decomposition of endoperoxide molecules with the aid of a material system composed of at least two molecules which contains at least one molecule forming an endoperoxide group an adaptation of a time progression of decomposition of the endoperoxide molecule is possible.

Singlet oxygen is produced within the context of the invention by the thermally activated decomposition of aromatic endoperoxide molecules which are embedded in the material systems used as pharmaceutical carriers such as for example liposomes, polymer nanoparticles or thin polymer films and have a sufficiently well adapted decomposition time $t_z$ in a sufficiently large number of sites. "Sufficiently adapted" means in particular that the endoperoxide molecules for the most part only decompose if these material systems are in a sufficiently short distance from the target region, for example in the interior of the cell or on the surface thereof, or the cells are located on the polymer film. It is crucial that the entire time progression of the release of singlet oxygen, in particular the distribution of the decomposition times $t_z$ occurring in the endoperoxide/material system, is adapted to the details of the particular use, so that the damage produced by the singlet oxygen molecules is sufficient to kill the cell. There must be enough endoperoxide molecules in the material system with decomposition times which are longer than the time $t_a$ for the take-up of the polymer into the cell (for example by endocytosis) or longer than the time for the settlement of a bacterium layer after an operation on an implant (e.g. tooth implant or artificial joint) on the material system applied as protective film.

With the aid of a confocal microscope, for example for liposomes with a diameter of 110 nm and polymer nanoparticles with a diameter of 140 nm, corresponding times $t_a$ were measured in specific cancer cells at 37° C., with a mean value range of several hours. On the other hand the decomposition times should not be too long, since the cells generally secrete the nanoparticles again after some time. Moreover, the damage regions caused by the singlet oxygen molecules must be produced in the target region of the cell in a shorter time interval than is required for it to be able to be eliminated again by repair mechanisms.

The first step in the adaptation of the half-life of the decomposition, or the corresponding distribution when there are several half-lives, consists of fixing a suitable combination of the components of the material system.

In a further advantageous embodiment the adaptation of the time progression of the decomposition of the endoperoxide molecules takes place by a chemical and/or a physical change of the functional structures present in the material system. All examples of applications which have already been produced show that it is possible by chemical and/or physical changes of these functional structures, which each consist of the molecule forming the endoperoxide and its immediate surrounding on the carrier material, to effect changes of the barrier level(s) for the decomposition and thus changes of the decomposition time(s), some of which amount to more than one order of magnitude, so that they can be used in order preferably to effect an adaptation of the overall progression of the decomposition to the desired purpose for which it is to be used, for example in tumour therapy.

A chemical change can take place for example by the addition of functional groups, such as for example methyl groups or hydroxyl groups, in the periphery of the molecule forming the endoperoxide or in the surrounding carrier material. Thus a polar hydroxyl group enables the formation of chemical bonds, such as for example hydrogen bonds.

In the case of physical changes to the functional structures, these generally involve a change of the site of the molecule forming the endoperoxide in the cage of the surrounding carrier material and/or a change of the cage or the cage wall.

The fundamental principle of the physical change of a special functional structure consisting of a molecule forming the endoperoxide and the cage of the surrounding polymer matrix includes the following procedure in the preparation. According to an endoperoxide formation procedure a decomposition process (preferably thermally activated) can proceed, wherein transformation processes give rise to a change of the functional structure. If after these preparatory steps an endoperoxide formation is again carried out, then this results in a changed decomposition time which may be attributed to the change of the barrier level for the decomposition associated with the geometric change of the functional structure. The details are apparent from the explanation of FIGS. 2 and 4.

In a further advantageous embodiment a first molecule or at least one further molecule of the material system constitutes a carrier material, wherein the carrier material is of organic and/or inorganic form. The carrier material has numerous molecules in its volume and has a suitable microscopic and macroscopic structure, wherein the endoperoxide molecules are adsorbed on the surface of the carrier material or embedded in the interior thereof. Moreover, the carrier material enables the transport of the molecules forming the endoperoxide to the target region or is itself to be regarded as the target region if for example it is applied as a protective film to an implant on which for example bacteria settle. It is conceivable to use liposomes, lipoproteins (in which conversion of the double bonds to single bonds has been carried out before use in the material system) or also polymers as organic carrier material.

In this case the production of the liposomes takes place by ultrasound treatment or by extrusion. The polymers may for example be present as polymer film which forms the carrier matrix or also as nanoparticles. Silica compounds for example or γ-aluminium oxide and similar materials used for adsorption are conceivable as inorganic carrier material.

In a further advantageous embodiment the molecule forming the endoperoxide of the material system is an aromatic compound. A naphthalene derivative such as for example 1,4-dimethylnaphthalene (DMN) or derivatives thereof, are preferably used as the molecule forming the endoperoxide. Endoperoxides are produced in the reaction of these naphthalene derivative with singlet oxygen. This reaction is designed to be reversible by a preferably thermally activated process. This means that, when heated, the endoperoxides decompose again into the aromatic molecule and the singlet oxygen on which they are based, wherein the decomposition times of the endoperoxides are generally different at a specific temperature. In endoperoxide formation the endoperoxide bridge is formed at the carbon atoms of the respective opposing points on the benzene ring at which additional substituents, such as for example a methyl group, are disposed. In this process singlet oxygen is captured and to a certain extent "stored". 1,4-dimethylnaphthalene may be categorised as harmless with regard to toxicity, since it is already contained in foods such as potatoes in order to prevent germination, and has been used as preservative when potatoes for consumption are stored.

Furthermore, it would also be conceivable to use specific aromatic compounds such as for example food colourings as the molecules forming the endoperoxide. Such aromatic compounds should preferably be categorised as harmless with regard to their toxicity.

In a further advantageous embodiment the aromatic compound forms endoperoxides by autoperoxidation, i.e. the compound itself acts as sensitiser (self-sensitised peroxidation). Autoperoxidation should be understood to mean the production and the capture of singlet oxygen with one and the same aromatic molecule. In this case the aromatic molecule is transformed by a suitable wavelength from the electronic ground state into the electronically excited singlet state. The transition into the triplet state of the aromatic molecule takes place by intersystem crossing. The excitation energy of the triplet state is transmitted to the molecular oxygen by energy transfer. In this case electronically excited singlet oxygen is produced, while the aromatic molecule returns to its ground state. This is interesting when it is advantageous that no additional photosensitising substance must be added to the material system. Meso-diphenyl helianthrenes are for example conceivable as aromatic compounds for such autoperoxidation.

In a further preferred embodiment a magnetic material is alternatively or additionally used in the material system. This is preferably an antiferromagnetic material.

The raising of the barrier in the example of PVB polymer films is preferably of interest for a specific application. Since these films can preferably be produced from completely amorphous polymer material with a thickness of less than 100 nm, they could be used for coating magnetic nanoparticles which are preferably present in the form of colloidal solutions as so-called ferrofluids.

In the therapeutic procedures currently being developed with these magnetic nanoparticles, these nanoparticles are guided by a magnetic field onto the desired region in the body, for example into the region of a tumour. In a coating these magnetic nanoparticles can preferably also transport an active substance specifically to the tumour (magnetic drug targeting), and moreover a local hyperthermia can be implemented up to a maximum of 46° C. by alternating magnetic fields. In this case by coating of the magnetic nanoparticles for example with amorphous polymer films which are doped with endoperoxide, singlet oxygen could be released in the region of a tumour. An adaptation of the barrier should include release of the singlet oxygen only at 46° C. and not already at 37° C., that is to say during transport of the nanoparticles.

This local release from the coating of a magnetic nanoparticle, which may be regarded as an implant, can also be transferred to other implants, for example to artificial joints, or to medical implants in general. It is of particular interest to apply coatings to medical implants (see for example: Hans Gollwitzer, Eine resorbierbare Poly-D,L-Laktid-Beschichtung zur Ausrüstung medizinischer Implantate, Dissertation, Technische Universität München, 2002).

In this case the main focus as a rule is on the release (elution) of antibiotics from the coating in order to achieve protection against bacteria, since bacterial colonisation can have the effect of infection-induced rejection of implants. When materials containing endoperoxide are used, bacteria, viruses and fungi can be killed not only in the case of implants but generally because of the anti-infectious action of the singlet oxygen released during decomposition.

With regard to the bactericidal action it is conceivable above all also to include bacteria with resistance (e.g. methicillin resistant bacteria *Staphylococcus aureus*, MRSA) or generally multi-resistant bacteria, since the bactericidal action of singlet oxygen with the aid of photodynamic therapy has already been demonstrated (for an overview see for example the article by Mariusz Grinholc et al, *Bactericidal effect of photodynamic therapy against methicillin-resistant staphylococcus aureus strain with the use of various porphyrin photo sensitizers*, Acta Biochemica Polonica 54 (2007) 665-870, online at: www.actabp.pl, and the literature referenced in this article.

It appears that the best way to use the invention with regard to the treatment of specific tumours is the combination with the method of the previously explained magnetic drug targeting including the local hyperthermia associated therewith. The most important details of this method can be learned from the article by Andreas S. Ziegler, "Nanopartikel -pharrnazeutische Zwerge mit Know-how", Medizinische Monatsschrift für Pharmazeuten 31 (2008), 455-468. Due to the combination with this method a selective action of the endoperoxide decomposition on the tumour can be achieved, wherein an enhanced release of singlet oxygen in the tumour can be achieved by the local temperature increase, since the magnetic nanoparticles are enriched in the tumour. In this case a polymer layer with a thickness less than the diffusion length in this polymer material should be applied to the surface of the magnetic nanoparticles (which themselves should have the smallest possible diameter), in any case the total diameter should be less than 200 nm, so that the particles are easily taken up in the cancer cell. The polymer should be biodegradable and resorbable and biocompatible. In this case a possible solution is for example to use a polymer which is otherwise usual for medical implants, such as for example poly-D,L-lactide (PDLLA), which is preferred as amorphous material in contrast to the semicrystalline poly-L-lactide (see: Hans Gollwitzer, "Eine resorbierbare Poly-D,L-Laktid-Beschichtung zur Ausrüstung medizinischer Implantate", Dissertation, Technische Universität München, 2002; page 19).

Dimethylnaphthalene (or a derivative) as dopant could be used as the molecule forming the endoperoxide. It may be expected that with the doped polymer all properties are achieved which were achieved with the amorphous polyvinylbutyral (PVB) described above, i.e. in particular an adaptation of the decomposition time (at 37° C. and then at the temperature from approximately 42° C. to 48° C. set during the hyperthermia phase), wherein this adaptation can take place with chemical and/or physical (see FIG. 4) changes to the functional structures of the polymer. For the adaptation of the time progression of the decomposition of the endoperoxide molecules it is important in this application that in particular during the transport to the cancer cell which takes place at and in the process of penetrating into the cancer cell the fewest possible endoperoxide molecules decompose, whereas in the cancer cell in the hyperthermia phase as much singlet oxygen as possible should be released in the magnetic field applicator (because of the heating due to the alternating magnetic field) for a treatment time of approximately more than one hour. In this case it should be noted that at elevated temperature certain repair mechanisms within the cancer cells are rendered inoperative and thus the cell-damaging action of the singlet oxygen is increased.

In a further advantageous embodiment a sensitiser is introduced removably into the material system. When the sensitiser is embedded into the carrier material (for example liposomes or polymer films) protoporphyrine derivatives, such as for example protoporphyrine IX-dimethyl ester, can usually be used, which are excited by a high-power LED or by a laser. In all polymer nanoparticles methylene blue is preferably used as sensitiser which is added to the aqueous suspension; in these cases the excitation preferably takes place with a diode laser (660 nm) or a corresponding LED. This is advantageous, since in this way the providing of the singlet oxygen for the endoperoxide formation preferably takes place outside the body, so that only the endoperoxide molecules are supplied to the organism. Thus the endoperoxide formation preferably takes place with spatial and/or temporal separation. Therefore the material systems can for example be produced on the day before the treatment of the patient or immediately before the treatment by light irradiation, preferably with the aid of the sensitiser, "activated" and provided as ointment additive or emulsion. Thus the patient is preferably not exposed to any irradiation during the treatment.

In a further advantageous embodiment the compound forming the endoperoxide with at least one molecule, which is disposed adjacent and is not part of the compound forming the endoperoxide, forms a chemical bond for example with the polymer material of the carrier. A chemical bond should be understood in particular as hydrogen bonds and covalent bonds, also including any type of intermolecular and intramolecular interactions.

In a further advantageous embodiment the method according to the invention—as already mentioned a number of times—is used in the pharmaceutical and/or medical fields. In general, in pharmaceutical therapy the aim is above all a targeted release of pharmaceuticals. In this case dosage forms are expected in particular to deliver a pharmacologically active substance under controlled conditions in a targeted manner at its region of action in the body ("drug targeting") and to release it there under defined conditions ("drug release"). Nanoparticles in particular constitute a dosage form by which this objective can be achieved. In this case the use of liposomes is just as conceivable as the use of aqueous polymer dispersions controlling the active substance release. Furthermore, coated nanoparticles of quickly degradable polymer are conceivable. All nanoparticles can be specially coated, for example with surfactants, so that they pass through the blood-brain barrier. Moreover, nanoparticles of ethyl cellulose and PVB (polyvinylbutyral) are conceivable, above all in the gastrointestinal tract, since ethyl cellulose is used in any case as excipient in the production of tablets and PVB is approved for the packaging of foodstuffs, i.e. it may pass into the gastrointestinal tract.

The use of material systems containing endoperoxide, which contain liposomes or nanoparticles in an ointment or emulsion, is conceivable as a further pharmaceutical/medical use for treatment of the skin (e.g. in the case of specific tumours or in the case of psoriasis). Here too the adaptation of the time progression of the thermally induced decomposition to the details of the use is important. In contrast to the use of polymer (nano)particles and inorganic (nano)particles—wherein the physical modification of the functional structures carried out according to FIG. 4 for adaptation of the decomposition time in a wide range can be used —in the case of liposomes the adaptation must be enabled by a selection of the chemical modifications. For the liposome material DMPC (1,2-dimyristol-L-α-phosphatidylcholine) which has been selected because it does not contain any double bonds, a half-life (with a monoexponential decomposition typical for endoperoxide-doped liposomes) of approximately one hour or eleven hours at 37° C. is obtained for example with the endoperoxides of DMN or DMNOH as dopant.

Furthermore it is conceivable for the method according to the invention also to be used in production technology, in particular if organic materials are used, since singlet oxygen is very reactive and reacts with many organic compounds (e.g. in oxidation processes, synthesis steps, changes to the double bonds, etc.). In this case too it is to be expected that the adaptation of the time progression of the endoperoxide decomposition (in the time range from seconds to minutes at localised temperatures up to over 100° C.) and of the corresponding singlet oxygen production to the requirements of the application in certain production steps of crucial significance. This applies for example to components of organic electronics, molecular electronics and organic optoelectronics (including the production of organic light emitting diodes, so-called OLEDs).

Furthermore the present invention comprises the use of a material system for producing singlet oxygen from at least two molecules, wherein at least one molecule is a compound forming endoperoxide.

Furthermore it would be conceivable for the previously mentioned nanoparticles of the material system, including the endoperoxide-doped liposomes, to be also bonded to antibodies by known processes and to be used for therapeutic purposes.

Moreover it is also conceivable in all applications (e.g. technical or medical), in addition to a thermally activated endoperoxide decomposition to induce the process for example by infrared light.

In general the material system can for example consist of pharmaceutical carrier materials which contain sensitiser molecules and Endoperoxide forming molecules separate from one another or consist for example of carrier materials, wherein only the molecules forming endoperoxide are embedded into the material, whilst the sensitiser is in solution for example separately, that is to say outside the carrier material. Furthermore the material system can consist of a carrier material which contains multichromophoric molecules, consisting of a sensitiser molecule and a minimum of 1 molecule forming endoperoxide which preferably represent a special type of autoperoxidation.

BRIEF DESCRIPTION OF THE DRAWINGS

Further advantageous embodiments are apparent from the appended drawings.

In the drawings.

DETAILED DESCRIPTION OF THE INVENTION

Figure 1:
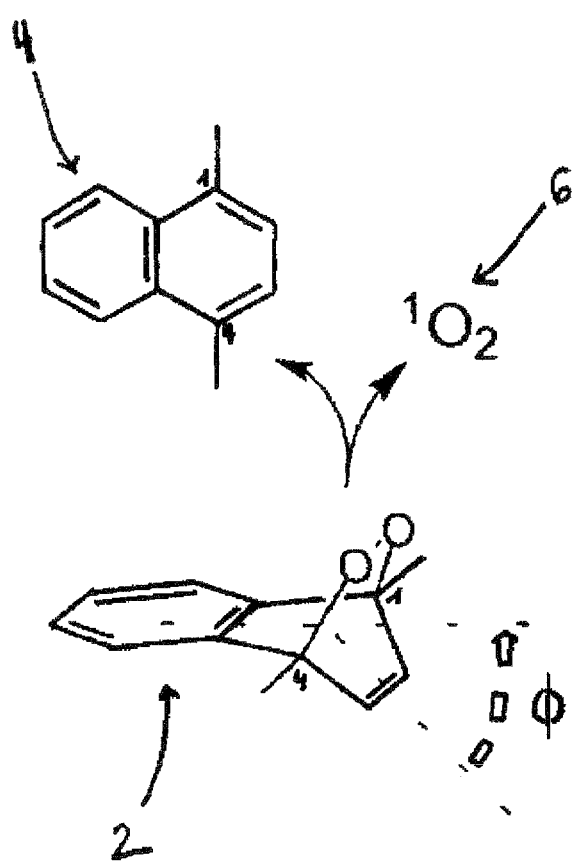
FIG. 1 shows a schematic representation of the thermolysis of a molecule forming endoperoxide (1,4-dimethylnaphthalene (DMN))

FIG. 1 shows a schematic representation of the thermolysis of a molecule forming endoperoxide. The endoperoxide molecule 2, in this case 1,4-dimethylnaphthalene endoperoxide, has an upwardly directed endoperoxide bridge at position 1 and 4 of the aromatics. In addition to the insignificantly low toxicity of DMN, a further important reason for using DMN-endoperoxide 2 is that in addition to the precise knowledge of the singlet oxygen production during decomposition the spatial structure is also very well known (see Wasserman et al. J. Par. J. Org. Chem. 70 (2005) 105-109). During the process of singlet oxygen release the non-planar DMN endoperoxide molecule 2 in which a ring is bent by the angle $\Phi$ decomposes again into the original aromatic and therefore planar DMN molecule 4, with singlet oxygen 6 split off, wherein the bending angle $\Phi$ must be bent back again.

Figure 2:
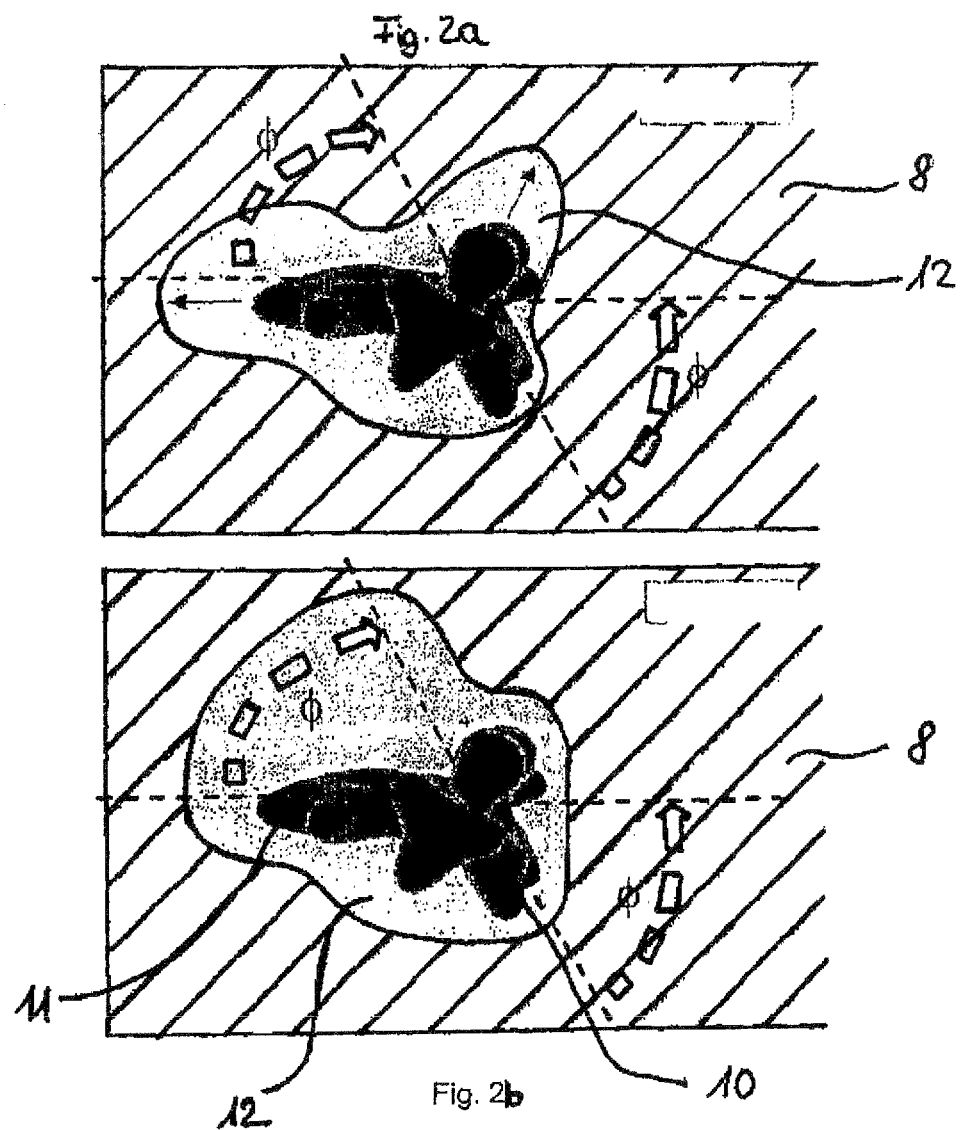
FIG. 2 shows a schematic space-filling model of the DMN endoperoxide molecule.

The energy barrier for this decomposition process is influenced by the interaction of the endoperoxide molecule 2 with the matrix 8 of the carrier material (FIG. 2a). This means that the DMN endoperoxide molecule 2 and the immediate vicinity of the surrounding carrier matrix 8 form—to a certain extent as a special site—a (supramolecular) functional structure. If liposomes are used as carrier material (which may be regarded as liquid crystal solid bodies) then the decomposition of the endoperoxide molecules 2 embedded in the liposome membrane can be changed by chemical changes of the functional structure. For example, bending back by the bending angle $\Phi$ can be hindered (or delayed) by the introduction of functional groups (as in FIG. 3).

On the other hand, in polymers—as already described above—physical changes of the functional structures also play an important part.

FIG. 2a shows the endoperoxide molecule 2 in a matrix 8 of the polymer material. For some of the measurements in order to demonstrate the increase in stabilisation, i.e. the increase in the decomposition times of endoperoxides due to physical changes to the functional structures, the polymer polyvinylbutyral (PVB) inter alia was used. PVB is a copolymer with various proportions of acetal, ester and hydroxyl groups. These are statistically distributed in the polymer chain and impede one another reciprocally due to their different spatial structure, so that PVB layers preferably always are present in amorphous form. Most of the side groups are polar and have permanent dipole moments.

The polymer PVB in this case is preferably used in the form of films and nanoparticles, whilst ethyl cellulose is preferably used in the form of nanoparticles. A description of the production of polymer nanoparticles is to be found for example in Sergey M. Borisov, et al, "Precipitation as a sample and versatile method for preparation of optical nanochemosensors", Talanta (2009) 1322-1330.

Areas with free volume regions 12 are produced in the carrier matrix 8 during the production of the polymer films or the polymer nanoparticles (for example by precipitation) because of the diffusing out of the solvent. Thus depending upon the local geometric conditions free volume regions of different size are produced in each functional structure. When the endoperoxide molecule 2 in the cage of the surrounding matrix 8 of the carrier material has no freedom of movement at the right end of the ring 10, then for example the left ring 11 can also be bent up, as shown in FIG. 2b, so that the original planar DMN structure 4 can also be produced again by this bending back.

Due to chemical changes, for example due to the introduction of functional groups, chemical bonds which delay bending back by the bending angle $\Phi$ can be formed between molecules of the carrier material 8 and the endoperoxide forming molecule 2. As already mentioned above, not only the chemical changes but also the physical changes are important. The fundamental principle of the physical change of a special functional structure consisting of a molecule forming the endoperoxide and the cage of the surrounding polymer matrix includes the following procedure in the preparation. According to an endoperoxide formation procedure a decomposition process (preferably thermally activated) can proceed, wherein transformation processes give rise to a change to the functional structure. If after these preparatory steps an endoperoxide formation is again carried out, then this results in a changed decomposition time which may be attributed to the change of the barrier level for the decomposition associated with the geometric change of the functional structure.

In a special method of preparation, with the aid of a first thermal cycle, that is to say with the carrying out of the decomposition process for a large proportion of the DMN endoperoxide molecules 2 which are present in this material 8 in two sites with different barrier levels, a raising of the barrier is produced in each case before the subsequent repeating of the endoperoxide formation process. In this first thermally activated decomposition process carried out extra for this special preparation, substantial excitation of vibrations of the molecules (or molecule groups) is produced in the cage wall 8 by the decomposition process and thus transformation processes can take place which result in changes of the functional structure. In PVB-polymer films these transformation processes in the cage wall lead to a reduction in the free volume 12 in the immediate surroundings of the molecules which form the endoperoxide and thus result in raising of the barriers for the renewed decomposition (because of the hindrance on bending back of the angle $\Phi$).

It should be mentioned that here only the simplest case of an endoperoxide molecule 2 located in a free volume 12 of the matrix 8 has been shown. Instead of this one endoperoxide molecule, it is also conceivable that for example functionalised molecule chains are present which are joined to one another via ester bonds or ether bonds and interact with the molecules of the matrix 8 of the carrier material.

Figure 3:
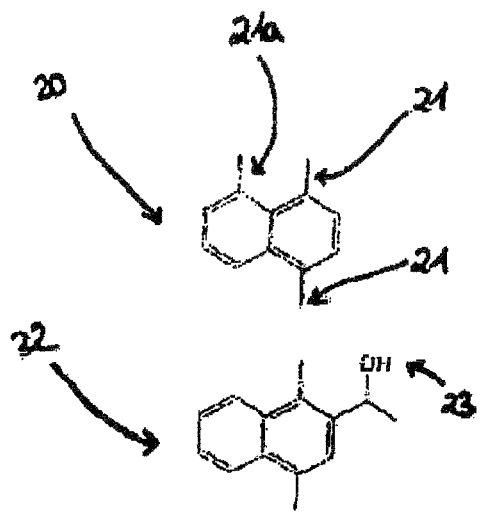
FIG. 3 shows further functionalised molecules forming endoperoxide.

FIG. 3 shows further molecules 20 and 22 forming the endoperoxide, wherein 20 shows the 1,4,5-trimethylnaphthalene (TMN) in which, in contrast to 1,4-dimethylnaphthalene, a further functional methyl group 21a is attached to the second ring. This further methyl group constitutes an additional hindrance for the above-mentioned bending back if the methyl groups can rotate freely, as is the case in the liquid crystal phase, wherein the TMN endoperoxide molecule fits between the paraffin-like chains of the membrane molecules. This additional steric hindrance produces a raising of the barrier for the decomposition of TMN endoperoxide 20 (by comparison with DMN endoperoxide in liposomes) and thus a raising of the half-life (to approximately 17 hours at 37° C.). Thus in TMN the half-life is adapted for a cancer therapy, since $t_z$ is clearly greater is than $t_a$ and killing of the cancer cells was ascertained for TMN endoperoxide not but for DMN endoperoxide in liposomes. This cytostatic effect was confirmed using the crystal violet test.

A further molecule 22 forming endoperoxide has an additional hydroxyl group which with the cage wall can form hydrogen bridges (preferably in PVB nanoparticles, in PVB films or ethyl cellulose nanoparticles), which likewise causes an increase in the decomposition times. The killing of cancer cells was also obtained with DMNOH endoperoxide in ethyl cellulose nanoparticles.

With DMNOH in ethyl cellulose nanoparticles it was also possible to show that the physical change of the functional structure can also be carried out in such a form that the decomposition is not increased by raising of the temperature but that it is sufficient to allow the process of endoperoxide formation to proceed more slowly (15 hours), so that during this long time sufficient decomposition processes also already take place at a lower temperature in order to change the functional structures correspondingly.

Figure 4A:
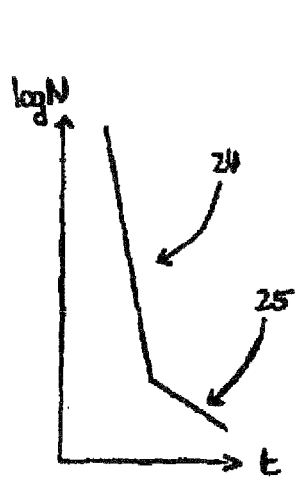
FIG. 4a shows in a diagram a schematically presented decomposition curve.
Figure 4B:
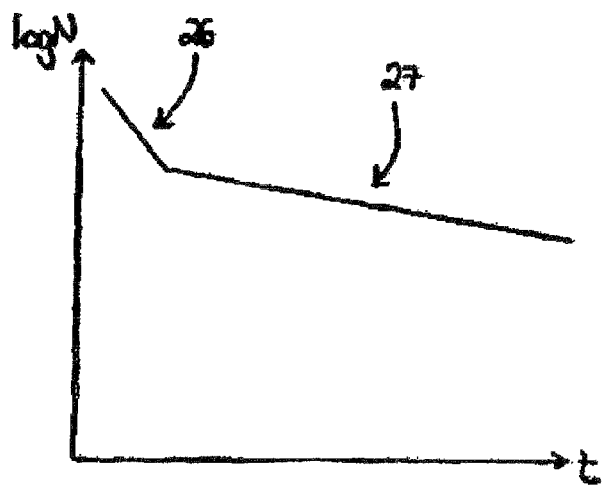
FIG. 4b shows in a diagram a changed schematically presented decomposition curve.

FIG. 4a shows the first decomposition over time of a molecule forming endoperoxide which is disposed in a polymer matrix. The abscissa shows the time, whereas the number of endoperoxide molecules is shown logarithmically on the ordinate. It will be apparent from a consideration of the decomposition curves of DMN endoperoxides in the PVB matrix that—in contrast to the monoexponential decomposition in all material systems in which an endoperoxide is embedded in liposomes—a biexponential decomposition is obtained in a good approximation. There is a statistical distribution of the functional structures, but in all polymer systems it is possible to use 2 functional structures as a good approximation. The entire decomposition curve is usually determined indirectly via the measurement of the fluorescence of the DMN molecules which reappear during decomposition of the endoperoxides.

In semi-logarithmic presentation, the two straight lines 24 and 25 are obtained (at 37° C.) as decomposition curves. In the evaluation it is apparent that the decomposition time, or more precisely the half-life of the decomposition from the curve 24 which is about 2 hours is only approximately 30% greater than that for DMN in organic solvent (at 37° C.), whereas the decomposition time from the curve 25 is already greater by approximately a factor 6. It is obvious to assign the curve 24 to a functional structure with a very large free volume, that is to say substantial freedom of movement for the bending back by the angle Φ, whilst the functional structures to be assigned to the curve 25 have a smaller free volume, so that progress of the decomposition is already slowed down. When the decomposition of the endoperoxides is largely completed, the previously described procedure for physical change of the functional structures has already been carried out. After renewed endoperoxide formation the decomposition curves 26 and 27, which in each case are again substantially shallower than curves 24 and 25 are obtained at 37° C.; the decomposition time of curve 27 is longer by more than a factor 30 than that of DMN in liquids, and the percentage of the slowly decomposing endoperoxide has become somewhat greater than in the case of curves 24 and 25.

The physical change of the functional structures means that the regions with a (large) free volume which after the original sample preparation are present directly alongside the DMN molecule as a state of non-equilibrium are reduced in size with the aid of the endoperoxide decomposition, During decomposition vibrations are excited which lead to transformation processes in which the molecules of the cage wall can move above all in the direction of the free volume. This leads to a raising of the barrier and thus to a lengthening of the decomposition time for the changed functional structures.

Results which are comparable with those using polymer films are obtained with DMN in polymer nanoparticles of PVB and of ethyl cellulose. When DMNOH (see FIG. 3) which has been produced on the basis of the synthesis described by I. Salto et al (J. Am. Chem. Soc. 107 (1985) 6329-6334) is used (see FIG. 3), because of the change of the chemical functional structure due to hydrogen bonds between DMNOH molecules and the OH groups of the ethyl cellulose, decomposition is obtained which is slower by the factor 3 than in the curve 24. After the same physical changes of the functional structure have been carried out (i e. endoperoxide decomposition) almost the same value was obtained as in the case of DMN. At the end of the new decomposition curve, after a third step of endoperoxide formation the decomposition can be measured again and a further increase in the decomposition time by approximately 50% can be obtained.

The applicant reserves the right to claim all the features disclosed in the application documents as essential to the invention in so far as they are individually or in combination novel over the prior art.

LIST OF REFERENCE NUMERALS

2 endoperoxide molecule
4 molecule forming endoperoxide
6 singlet oxygen
8 matrix
10 right ring of the endoperoxide molecule
11 left ring of the endoperoxide molecule
12 free volume
20 TMN
21 methyl group
21a further methyl group
22 DMNOH
23 hydroxyl group
24 fast endoperoxide decomposition
25 slow endoperoxide decomposition
26 changed fast endoperoxide decomposition
27 changed slow endoperoxide decomposition

The invention claimed is:
1. A method for lengthening and/or adapting decomposition of 1,4 dimethylnaphthalene endoperoxide molecules or derivatives thereof, and consequent singlet oxygen release for specific needs comprising the steps of:
  a) providing polymer material system,
  b) bringing precursors for 1,4 dimethylnaphthalene endoperoxide molecules in cages formed by said polymer material system, wherein said cages differ in its geometry, thereby forming at least two different types of sites providing different barrier level for decomposition of said endoperoxide molecules located within one of said sites, wherein said precursors comprise a planar aromatic ring system and wherein parts of chains in said polymer material system form walls of the cages in which the precursors are arranged, thereby forming at least two different supramolecular functional structures;
  c) formation of 1,4 dimethylnaphthalene endoperoxide molecules in said sites by a sensitizer-assisted process, wherein the formation of 1,4 dimethylnaphthalene endoperoxide molecules causes bending of said previously planar aromatic ring system,
  d) activated decomposition of at least a part of 1,4-dimethylnaphthalene endoperoxide molecules in said sites, whereby said activation of decomposition including thermal activation or IR-activation is providing a non-thermal local excitation energy for at least one part of a polymer chain in said cage wall which is shifting into an interior volume of said site, thereby reducing its free volume with respect to bending back of 1,4-dimethylnaphthalene endoperoxide molecules, whereby this reduction is increasing an energy barrier for said decomposition by hindering said bending back,
  e) repeating steps c) and d) successively until a mean energy barrier for decomposition of first sites including 1,4 dimethylnaphthalene endoperoxide molecules located in first sites of said polymer material system providing a first barrier level for decomposition of said endoperoxide molecules is increased so that at a given temperature an average decomposition time of said first site of endoperoxide molecules is lengthened up to a factor of 30 in comparison to an average decomposition time of said 1,4 dimethylnaphthalene endoperoxide molecules in a liquid at said given temperature, whereas for second sites including said endoperoxide molecules located in said polymer material system providing a second barrier level for decomposition of said endoperoxide molecules an average decomposition time is lengthened by only a factor up to two in comparison to said average decomposition time of said endoperoxide molecules in a liquid at said given temperature,
thereby forming a functional material system, comprising said first and second sites, whereby said two average decomposition times of said two sites are different up to at least a factor of 15.

2. The method as claimed in claim 1, further comprising performing said activated decomposition of step d) and said formation step c) simultaneously, whereby a content of said first sites is increased with respect to a content of said second sites and wherein this increase is performed until all of said sites are belonging to said first sites with said average lengthening up to a factor of 30 or until requirements of specific needs concerning conservation of a rest of said second sites are fulfilled.

3. The method as claimed in claim 1, wherein the polymer material is selected from the group consisting of an organic biocompatible polymer, polyvinylbutyral, ethyl-celluose, a biodegradable polymer, a bioresorbable polymer and polylactide, and wherein the polymer material is present in a form of a film and/or a nanoparticle and/or a coating of a nanoparticle.

4. The method as claimed in claim 1, wherein the functional material system further comprises magnetic nanoparticles, so that a spatially and temporally selective effect of the endoperoxide decomposition can be achieved based on a local energy transfer by an alternating magnetic field resulting in a local enhancement of temperature.

5. The method as claimed in claim 1, wherein the 1,4 dimethylnaphthalene endoperoxide molecule is a derivative of 1,4 dimethylnaphthalene endoperoxide which is
  i) comprising independently from each other at least one side chain, at least one further methyl group or derivatives thereof, at least one hydroxyl group, at least one ethyl group or derivatives thereof, and/or
  ii) is bound by a linker molecule including an ether or ester bond or by a hydrogen bond to a chain of the polymer material system forming walls of the cage in which the 1,4 dimethylnaphthalene endoperoxide molecule is located.

6. The method as claimed in claim 1, wherein a sensitiser is removably inserted in the functional material system.

7. The method as claimed in claim 1, wherein a sensitiser is joined to at least a precursor molecule by a chemical bond, wherein the precursor molecule can be converted to the 1,4 dimethylnaphthalene endoperoxide molecule.

8. The method as claimed in claim 1, wherein singlet oxygen released by the decomposition of the 1,4 dimethylnaphthalene endoperoxide molecules or the derivatives thereof in said polymer material system is used in specific applications known by photodynamic therapy, including treatment of psoriasis.

9. The method as claimed in claim 1, wherein the adaption of the decomposition of the 1,4 dimethylnaphthalene endoperoxide molecules takes place by a physical and/or a chemical change said supramolecular functional structures present in the functional material system.

10. The method as claimed in to claim 1, wherein the decomposition of the 1,4 dimethylnaphthalene endoperoxide molecules is induced by irradiation.

11. The method as claimed in claim 10, wherein the irradiation comprises infrared and/or ultraviolet radiation.

12. The method as claimed in claim 1, wherein the decomposition of 1,4 dimethylnaphthalene endoperoxide molecules in said polymer material system is used in medical and/or pharmaceutical field.

13. The method as claimed in claim 1, wherein said precursor molecule, which can be converted to a 1,4 dimethylnaphthalene endoperoxide molecules, is chemically bond to at least one molecule which is disposed within a cage wall formed by the polymer material system.

14. The method as claimed in claim 1, further comprising the steps of:
  f) bringing the 1,4 dimethylnaphthalene endoperoxide molecules in a distance of less than 1 µm from a target region and/or enriching its concentration in a distance of less than 1 µm from the target region, and
  g) inducing of the decomposition of the endoperoxide of 1,4-dimethylnaphthalene molecules for generating a flux of singlet oxygen into the target region.

15. The method as claimed in claim 14, wherein in step f) a concentration of said endoperoxide of 1,4-dimethylnaphthalene molecule is enriched in a tumour cell by endocytosis.

16. The method as claimed in claim 14, wherein said decomposition of the 1,4 dimethylnaphthalene endoperoxide molecule is accelerated by local enhancement of temperature.

17. The method as claimed in claim 14, wherein step f) is performed by aid of antibody technology, including parts of said technologies.

18. The method as claimed in claim 14, wherein step f) is performed by allowing multiresistant bacteria to settle on a surface of an implant, which surface layer comprises said 1,4 dimethylnaphthalene endoperoxide molecules in said polymer material system, wherein step g) is performed after completion of the settlement.

19. The method as claimed in claim 14, wherein said functional material system further comprises magnetic nanoparticles and wherein step f) is performed by magnetic drug targeting.

20. The method as claimed in claim 1, wherein said decomposition of 1,4 dimethylnaphthalene endoperoxide molecules in said polymer material system is used for therapy of a tumour and/or leukaemia.

21. The method as claimed in claim 1, wherein said decomposition of 1,4 dimethylnaphthalene endoperoxide molecules in said polymer material system is used for antimicrobial treatment, including treatment of multiresistant bacteria and/or virus and/or fungus.

22. The method as claimed in claim 21, wherein said functional material system is applied on the surface of a medical implant.

23. Use of a method for lengthening and/or adapting decomposition of 1,4 dimethylnaphthalene endoperoxide molecules or derivatives thereof, and subsequent controlled singlet oxygen release time periods for specific needs for anti-microbial treatment including a surface of an implant, whereby the method comprises the steps of:
   a) providing polymer material system,
   b) bringing precursors for 1,4 dimethylnaphthalene endoperoxide molecules in cages formed by said polymer material system, wherein said cages differ in its geometry, thereby forming at least two different types of sites providing different barrier level for decomposition of said endoperoxide molecules located within one of said sites, wherein said precursors comprise a planar aromatic ring system and wherein parts of chains in said polymer material system form walls of the cages in which the precursors are arranged, thereby forming at least two different supramolecular functional structures;
   c) formation of 1,4 dimethylnaphthalene endoperoxide molecules in said sites by a sensitizer-assisted process, wherein the formation of 1,4 dimethyl naphthalene endoperoxide molecules causes bending of said previously planar aromatic ring system,
   d) activated decomposition of at least a part of 1,4-dimethylnaphthalene endoperoxide molecules in said sites, whereby said activation of decomposition including thermal activation or IR-activation is providing a non-thermal local excitation energy for at least one part of a polymer chain in said cage wall which is shifting into an interior volume of said site, thereby reducing its free volume with respect to bending back of 1,4-dimethylnaphthalene endoperoxide molecules, whereby this reduction is increasing an energy barrier for said decomposition by hindering said bending back,
   e) repeating steps c) and d) successively until a mean energy barrier for decomposition of first sites including 1,4 dimethylnaphthalene endoperoxide molecules located in first sites of said polymer material system providing a first barrier level for decomposition of said endoperoxide molecules is increased so that at a given temperature an average decomposition time of said first site of endoperoxide molecules is lengthened up to a factor of 30 in comparison to an average decomposition time of said 1,4 dimethylnaphthalene endoperoxide molecules in a liquid at said given temperature, whereas for second sites including said endoperoxide molecules located in said polymer material system providing a second barrier level for decomposition of said endoperoxide molecules, an average decomposition time is lengthened by only a factor up to two in comparison to said average decomposition time of said endoperoxide molecules in a liquid at said given temperature, thereby forming a multi-functional material system, comprising said first and second sites whereby said two average decomposition times of said two sites are different up to at least a factor of 15, wherein activated decomposition of step d) and said formation step c) are also performed simultaneously, whereby a content of said first sites is increased with respect to a content of said second sites and wherein this increase is performed until all of the sites are belonging to said first sites with said average lengthening up to a factor of 30 or until requirements of specific needs concerning conservation of a rest of said second part are fulfilled, wherein the functional material system further comprises magnetic nanoparticles, so that a spatially and temporally selective effect of the endoperoxide decomposition can be achieved based on a local energy transfer by an alternating magnetic field resulting in a local enhancement of temperature.

* * * * *

UNITED STATES PATENT AND TRADEMARK OFFICE
CERTIFICATE OF CORRECTION

PATENT NO. : 9,969,617 B2  
APPLICATION NO. : 13/384749  
DATED : May 15, 2018  
INVENTOR(S) : Bogner et al.

Page 1 of 1

It is certified that error appears in the above-identified patent and that said Letters Patent is hereby corrected as shown below:

On the Title Page

Column 1, item (54), title of invention:  
"ADAPTION" should be --ADAPTATION--.

Column 1, item (76), Inventor city/country of residence:  
"Österreich (DE)" should be --Gallneukirchen (AT)--.

Column 1, item (*), Notice:  
"0 days. days." should be --0 days.--.

Column 1, item (30), Foreign Application Priority Data:  
"10 2009 034 279" should be --10 2009 034 279.6--.

Signed and Sealed this  
Twenty-fifth Day of September, 2018

Andrei Iancu  
*Director of the United States Patent and Trademark Office*